United States Patent [19]

Schickling et al.

[11] Patent Number: 5,171,305
[45] Date of Patent: Dec. 15, 1992

[54] LINEAR EVERSION CATHETER WITH REINFORCED INNER BODY EXTENSION

[75] Inventors: David P. Schickling, Laguna Hills; Guy R. Lowery, Mission Viejo; Steven R. Bacich, Laguna Niguel; David M. Ciulei, Huntington Beach; Gary Woker, Escondido, all of Calif.

[73] Assignee: Imagyn Medical, Inc., Laguna Niguel, Calif.

[21] Appl. No.: 780,098

[22] Filed: Oct. 17, 1991

[51] Int. Cl.$^5$ .............................................. A61M 5/00
[52] U.S. Cl. ............................................ 604/271; 604/282
[58] Field of Search ................................. 604/96–103, 604/271, 280–283; 606/192–194, 196

[56] References Cited

U.S. PATENT DOCUMENTS

| | | | |
|---|---|---|---|
| 3,500,819 | 3/1970 | Silverman | 604/271 X |
| 3,982,544 | 9/1976 | Dyck | 604/271 |
| 4,271,839 | 6/1981 | Fogarty et al. | |
| 4,530,698 | 7/1985 | Goldstein et al. | 604/271 |
| 4,604,994 | 8/1986 | Shook | |
| 4,630,609 | 12/1986 | Chin | |
| 4,646,719 | 3/1987 | Neuman et al. | |
| 4,784,158 | 11/1988 | Okimoto | 128/771 |
| 4,990,138 | 2/1991 | Bacich et al. | |
| 5,041,089 | 8/1991 | Mueller et al. | 604/96 |
| 5,074,845 | 12/1991 | Miraki et al. | 604/101 |

OTHER PUBLICATIONS

"The Ins and Outs Of Toposcopy and The Everting Catheter", D. R. Shook, *SOMA*, Jul. 1987, pp. 22–27.
"Everting (Toposcopic) Catheter for Broad Clinical Application", D. R. Shook et al; *Journal of Biomechanical Engineering*, May 1986 vol. 108, pp. 168–174.

*Primary Examiner*—John D. Yasko
*Assistant Examiner*—Adam J. Cermak
*Attorney, Agent, or Firm*—Gordon L. Peterson

[57] ABSTRACT

A catheter comprising an elongated catheter body having a lumen with a distal opening, an elongated inner tube having a flexible distal end portion and a flexible everting element coupled to the catheter body and the inner tube so that the everting element can be inverted and everted to the distal opening. The inner tube has an inner tube lumen which extends through the distal end portion of the inner tube. The distal end portion of the inner tube includes a flexible tubular layer and a flexible reinforcing layer which reinforces the tubular layer and inhibits radial collapse of the inner tube lumen in the distal end portion of the inner tube.

21 Claims, 4 Drawing Sheets

LINEAR EVERSION CATHETER WITH REINFORCED INNER BODY EXTENSION

BACKGROUND OF THE INVENTION

An everting catheter is commonly used to gain access to various regions of the human body. With the catheter properly placed, an instrument, such as an endoscope or other elongated member can be passed through the lumen of the catheter to carry a desired function adjacent the distal end of the catheter.

An everting catheter typically includes an elongated catheter body having a lumen with a distal opening, an elongated inner tube having a flexible distal end portion and a flexible everting element coupled to the catheter body and to the inner tube. With this construction, the everting element can be inverted and everted through the distal opening. The inner tube, which may be considered as an inner catheter, has an inner tube lumen extending through the distal end portion of the inner tube. With the catheter properly positioned within a patient, an endoscope or other instrument is advanced through the inner tube lumen to the desired body region. Alternatively or in addition thereto, a fluid, such as a drug, can be infused through the inner tube lumen or the inner tube lumen may be used for aspiration.

To enable the distal end portion of the inner tube to conform to curved or tortuous body passages, it is important that the distal end portion of the inner tube be flexible. On the other hand, the distal end portion of the inner tube cannot be so flexible that it collapses radially inwardly to occlude or partially occlude the inner tube lumen because this lumen must remain open for the passage of a medical instrument or for infusion or aspiration purposes. For example, if the distal end portion of the inner tube is not sufficiently resistant to radial compressive forces, it may collapse, or partially collapse, due to various factors, such as the internal fluid pressure within the everting element or it may kink in navigating a curve within the body. Unfortunately, the requirements for flexibility and rigidity against radial compressive loads are inconsistent, and the prior art techniques of which we are aware have not satisfactorily achieved both flexibility and resistance to radial inward loads.

Another problem with everting catheters is that retraction or proximal movement of the inner tube too far may damage or even rupture the thin, flexible everting element. When this occurs, the catheter is effectively rendered useless for its intended purposes and cannot be safely used.

SUMMARY OF THE INVENTION

This invention solves these problems by providing a catheter having an inner tube with a distal end portion which is both flexible and resistant to radial inward loads. In addition, damage to the everting element as a result of retracting the inner tube too far is prevented.

With this invention, the distal end portion of the inner tube is rendered both flexible and resistant to radial inward loads by employing a flexible tubular layer and a flexible reinforcing layer. The reinforcing layer reinforces at least a region of the tubular layer and inhibits radial collapse of at least a region of the inner tube lumen in the distal end portion of the inner tube.

This construction has a number of other advantages. For example, the tubular layer may be used to define a smooth wall for the inner tube lumen. Preferably, the tubular layer includes lubricious material which defines at least a portion of the surface of the inner tube lumen. The tubular layer may advantageously be constructed of a polymeric material. In a preferred construction, the inner tube includes a proximal section which is more rigid than the distal end portion and is attached to the distal end portion.

The reinforcing layer may also be of various different constructions. Generally, the reinforcing layer may include at least one elongated element which is wound circumferentially of the tubular layer. Although the reinforcing layer may include a braid, it preferably includes a coil spring. A spring is preferred because it provides substantial resistance to radial inward loads and can readily flex to enable the distal end portion of the inner tube to negotiate curves. To enhance flexibility while increasing resistance to radial loads, the spring is preferably tightly wound, and the turns of each coil are preferably normally in engagement. Any separation of the coils on the outside of a curve being negotiated by the distal end portion of the inner tube should be slight to not provide an unsupported gap of sufficient length to allow kinking or radial collapse of the inner tube. Although flat wire can be used for the coil spring, preferably the wire is round or D-shaped because round or D-shaped wire can be more flexible. Round wire is preferred because it is less expensive than D-shaped wire.

The region of the distal end portion of the inner tube which is reinforced to inhibit the collapse of the inner tube lumen may be the entire length of, or substantially the entire length of, the distal end portion of the inner tube. However, in a broader sense, less than the entire length of the distal end portion of the inner tube needs to be reinforced. In this regard, in a fully everted position, a major length of the distal end portion of the inner tube extends distally of the distal opening. This invention preferably provides for the reinforcement of the tubular layer adjacent the distal opening in the fully everted position to inhibit radial collapse of the inner tube lumen in that same region. The region of the inner tube which is adjacent the distal opening in the fully everted position is important to reinforce because of the reduction in strength of the catheter at the location where the inner tube projects beyond the catheter body.

Different physical relationships between the reinforcing layer and the tubular layer can be employed. For example, the reinforcing layer may be embedded in the tubular layer. This has the advantage of enabling the tubular layer to provide smooth inner and outer surfaces for the distal end portion of the inner member, and it automatically serves to couple the two layers together. However, in a preferred construction, the reinforcing layer receives and surrounds the tubular layer. This enables the reinforcing layer to flex without being as constrained as it would be if it were within the tubular layer. Consequently, flexibility is improved without degrading resistance to radial inward loads.

When the reinforcing layer receives the tubular layer, it is desirable, but not essential, to provide a coating, such as a polymeric coating, on at least a portion of the reinforcing layer. The coating preferably completely circumscribes at least a portion of the spring. The polymeric coating may be provided by dipping the reinforcing layer in, for example, urethane and/or by a region of the everting element. Such region of the everting element may be heat shrunk over the reinforcing layer.

So that the inner tube or similar inner member cannot be moved proximally sufficiently to rupture the everting element, this invention provides engageable stops which limit the proximal movement of the inner tube within the lumen of the catheter body. This feature may be provided in an everting catheter whether or not such catheter employs the tubular layer and flexible reinforcing layer.

Although the stops can be provided in different ways, it is important that the stops do not inhibit the fluid pressure used for eversion or inhibit longitudinal movement of the inner tube. This can be accomplished, for example, by employing a fitting coupled to the proximal end portion of the catheter body and having one of the stops carried by the fitting and another of the stops carried by the inner tube. More specifically, the fitting preferably has a passage extending through it, and the inner tube extends through the passage. One of the stops can advantageously be provided internally of the fitting and within the passage. In a preferred construction, the stop in the passage has an opening through which the inner tube extends, and this opening is too small to permit the stop carried by the inner tube to pass through the opening.

The invention, together with additional features and advantages thereof may best be understood by reference to the following description taken in connection with the accompanying illustrative drawing.

BRIEF DESCRIPTION OF THE DRAWINGS

FIGS. 4 and 5 are sectional views similar to FIGS. 2 and 3 showing one form of this invention. In FIG. 4, the everting element is fully everted, and in FIG. 5, the everting element is fully inverted.

DESCRIPTION OF THE PREFERRED EMBODIMENT

Figure 1:
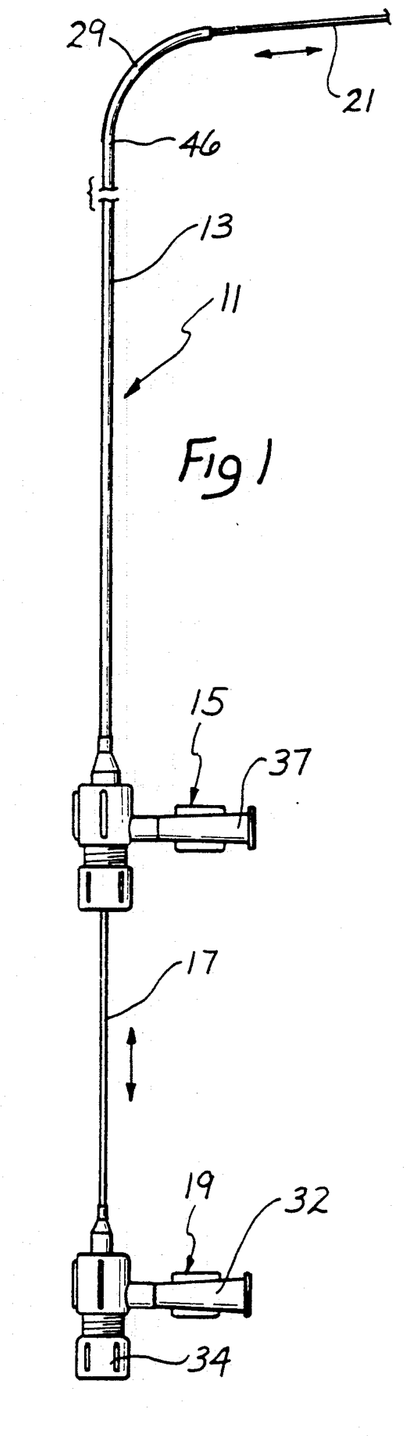
FIG. 1 is a plan view illustrating one form of catheter constructed in accordance with the teachings of this invention.

FIG. shows an everting catheter 11 which is particularly adapted for accessing the fallopian tubes; however, it should be understood that the features of this invention are also applicable to other kinds of catheters.

Figure 9:
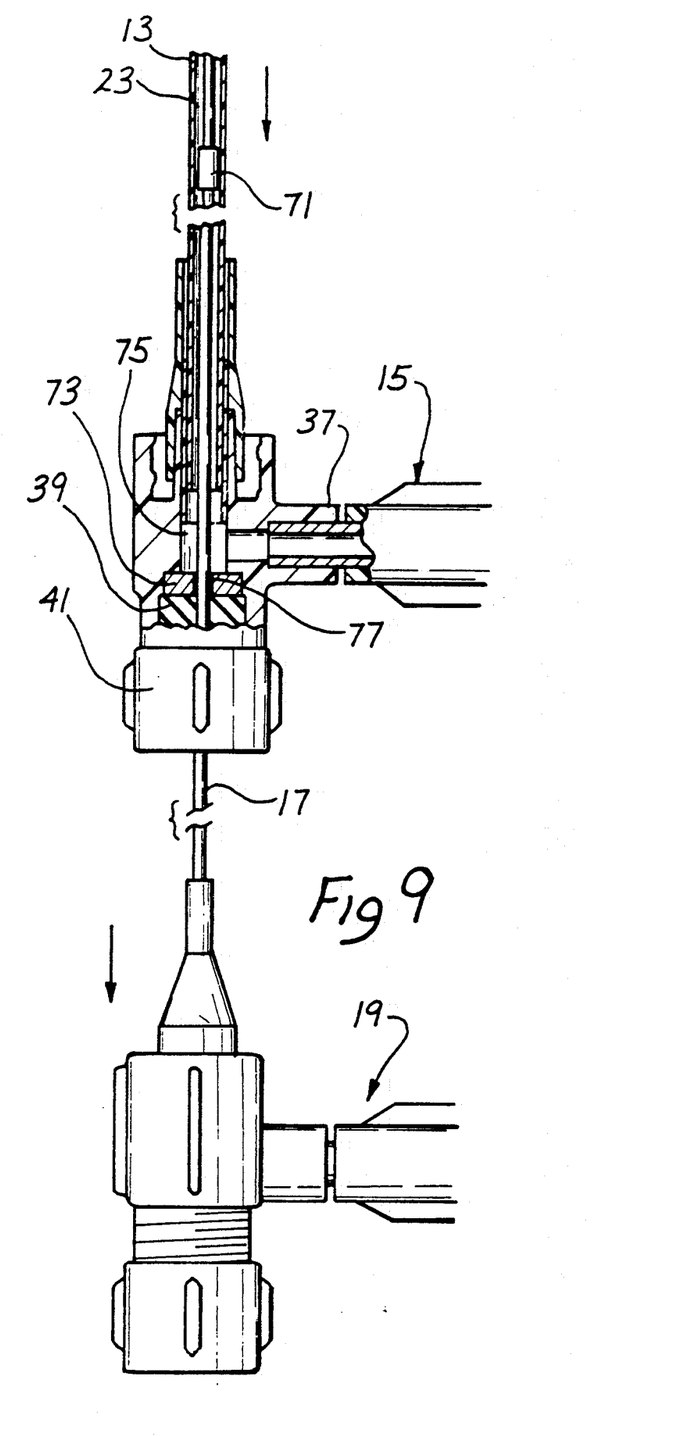
FIG. 9 is a plan view partially in section of a proximal region of the catheter illustrating one way in which stops can be used to limit the proximal movement of the inner member.

The catheter 11 generally comprises a catheter body 13, a proximal fitting 15, an inner tube 17, an inner tube fitting 19 and an everting element 21. The catheter body 13 is elongated and flexible and has a through lumen 23 (FIGS. 4 and 5) which extends axially all the way through the catheter body from a proximal end of the body at the proximal fitting 15 to a distal end 25 of the catheter body (FIGS. 4 and 5) where the lumen opens at a distal opening 27. The proximal end of the catheter body 13 is coupled to the proximal fitting 15 as shown in FIG. 9. The entire catheter body 13 is constructed of a flexible biocompatible material. For example, the catheter body 13 may be constructed of a flexible, biocompatible polymeric material, such as nylon, polyethylene, polyurethane or silicone. The catheter body 13 may be constructed of one or more sections as desired.

The catheter body 13 has a distal end portion 29 which, in its unstressed condition, may be straight or of any other shape designed to best gain access to a desired region of the body. In this embodiment, the distal end portion 29 is curved and forms a portion of a circular arc in the unstressed condition.

Figure 4:
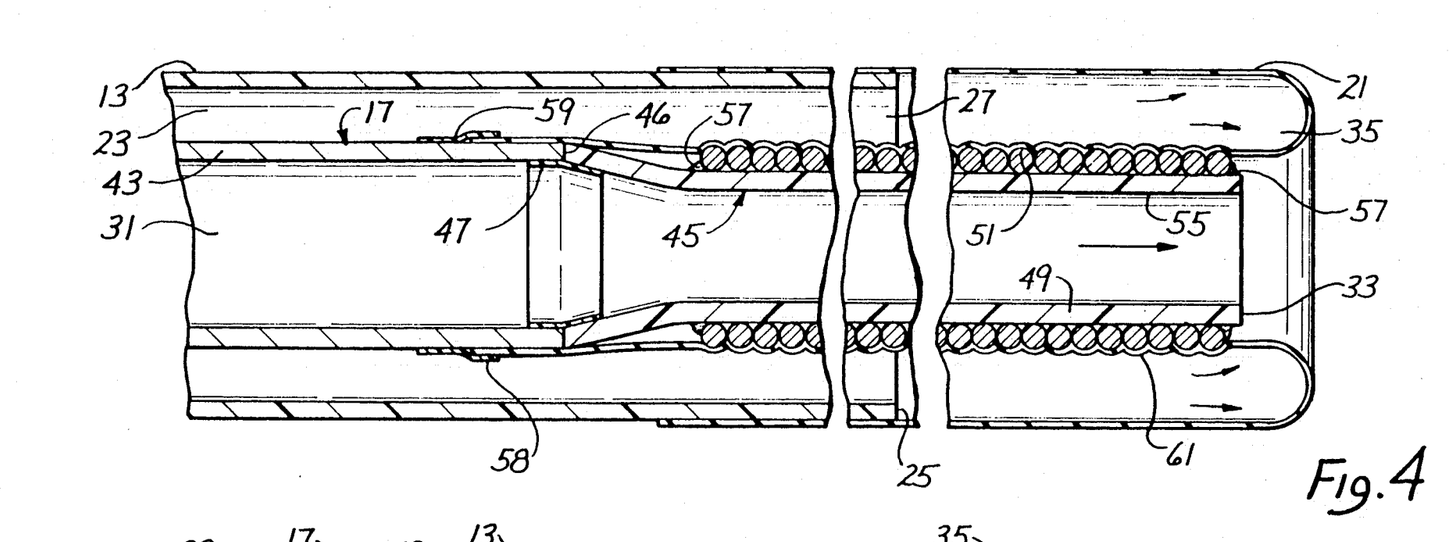
Figure 5:
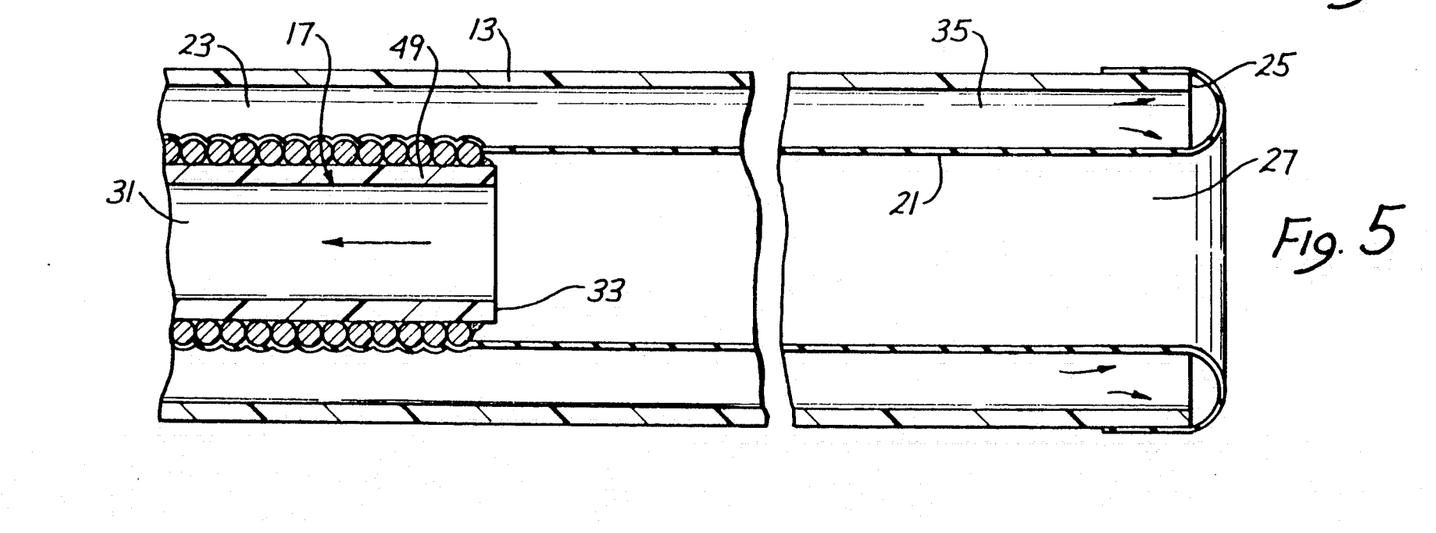

The inner tube 17 has an inner tube lumen 31 which extends longitudinally completely through the inner tube from a proximal end of the inner tube 17 at the inner tube fitting 19 to a distal end 33 (FIGS. 4 and 5) of the inner tube. The proximal end of the inner tube 17 is coupled to one leg of the inner tube fitting 19. The inner tube fitting 19 also has an injection leg 32 which can be used, for example, for irrigation fluid, a contrast dye, drugs or for aspiration. Any media infused through the leg 32 passes through the inner tube lumen 31 and out through the distal end 33. The fitting 19 has a leg 34 which provides a port for the introduction of a variety of medical instruments, such as an endoscope. The everting element 21 is a thin, flexible membrane which is constructed of a suitable polymeric material. As shown in FIGS. 4 and 5, the everting element 21 is bonded as by an adhesive to an outer surface of the catheter body 13 adjacent the distal end 25 and to an outer surface of the inner tube 17. This forms a chamber 35 which communicates with the lumen 23 of the catheter body 13 outside of the inner tube 17. As shown in FIG. 9, the lumen 23 communicates with an injection leg 37 of the proximal fitting 15 so that an inflation media can be supplied to the lumen 23 and the chamber 35. A seal 39 carried by the proximal fitting 15 prevents the inflation media from exiting through a leg 41 of the fitting 15.

With this construction, an inflation media can be supplied to the chamber 35 to control the inversion and eversion of the everting element 21. The inner tube 17 can be moved axially within the lumen 23 to also control the inverting and everting movements of the everting element 21.

Figure 2:
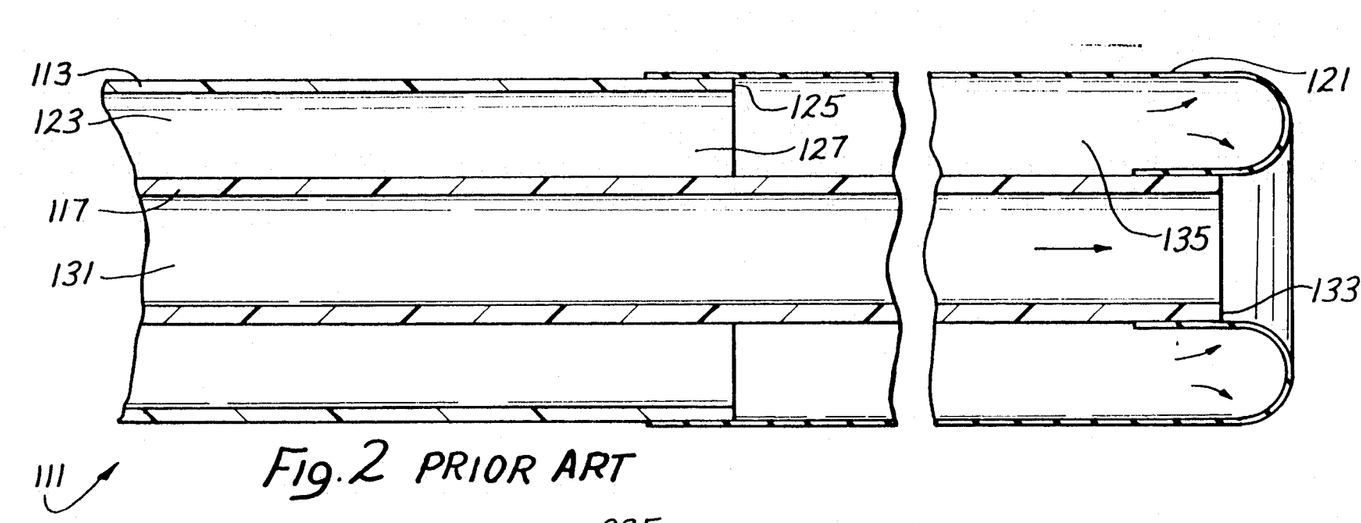
FIGS. 2 and 3 are enlarged, longitudinal sectional views through distal regions of two prior art everting catheters in the everted position.

FIG. 2 shows the distal tip region of a prior art catheter 111. Portions of the catheter 111 corresponding to portions of the catheter 11 are designated by corresponding reference numerals preceded by the number "1." In FIG. 2, the inner tube 117 is flexible at least in the region illustrated and may be constructed of a flexible, biocompatible polymeric material. The everting element 121 is bonded to an outer surface of the catheter body 113 and an outer surface of the inner tube 117 closely adjacent the distal end 133. As described above, one problem with this construction is that the illustrated region of the inner tube 117 tends to collapse radially inwardly in response to the pressure in the chamber 135, and/or it may kink as a result of negotiating curves within the human body.

Figure 3:
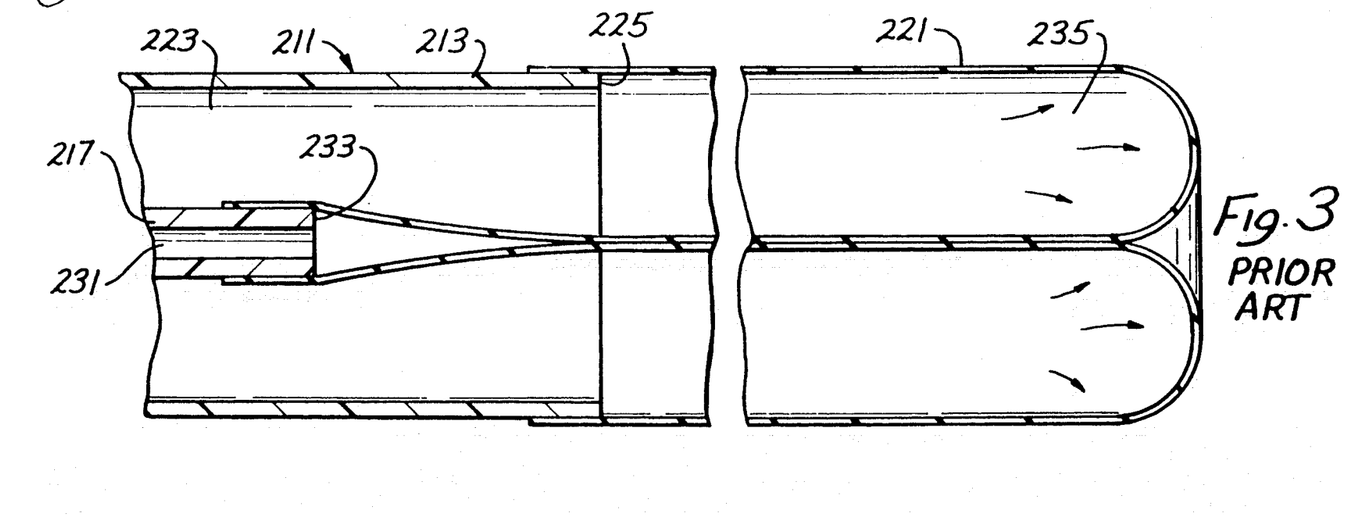

FIG. 3 shows another prior art construction for the distal tip region. Portions of the device shown in FIG. 3 corresponding to portions of the catheter 11 are designated by corresponding reference numerals preceded by the number "2." The prior art construction of FIG. 3 is essentially the same as the prior art construction of FIG. 2, except that the distal end 233 of the inner tube 217 is within the lumen 223 in the everted position. With the construction of FIG. 3, there is no open lumen through the everting element 221 in the everted position. Consequently, in order to pass an instrument through the inner tube lumen 231 and the everted everting element 221, it is necessary to apply negative internal pressure in the chamber 235 to allow passage of the instrument through the everted everting element.

The present invention avoids the problems with the construction of FIG. 2 and the additional equipment and steps required in connection with the device of FIG. 3. As shown in FIGS. 4 and 5, the inner tube 17 includes a proximal section 43 and a distal end portion 45 suitably interconnected at a juncture 46 as by a coupling sleeve 47 which is adhered to both the proximal section and the distal end portion. The proximal section 43 is more rigid than the distal end portion 45 and may be constructed, for example, of stainless steel. The coupling sleeve 47 may be constructed of a material, such as polyimide which can be adhered to both the material of the proximal section 43 and the material of the distal end portion 45. A proximal portion of the tubular layer 49 is flared radially outwardly adjacent the juncture 46 to provide a diameter which matches the diameter of the proximal section 43.

The distal end portion 45 is flexible and provides substantial resistance to radial, inward loads. For this purpose, the distal end portion 45 comprises multiple layers. More specifically, the distal end portion 45 includes a flexible, tubular layer 49 and a flexible reinforcing layer 51. The reinforcing layer 51 reinforces the tubular layer 49 and inhibits radial collapse of the inner tube lumen 31 in the distal end portion 45 of the inner tube 17.

The juncture 46 should be located sufficiently, proximally so that a sufficient length of the inner tube 17 is flexible. For example, if the distal end portion 29 of the catheter 11 is curved as shown in FIG. 1, the juncture 46 should be located proximally of the proximal end of the curve 29 in the everted position so that the more rigid proximal section 43 does not enter and straighten the curved distal end portion 29. For convenience of illustration, the scale of FIG. 1 has not been maintained in FIGS. 4 and 5, and the catheter 11 is shown as straight in these two figures.

The tubular layer 49 provides a smooth inner surface 55 for the surface of the inner tube lumen 31. The tubular layer 49 is preferably constructed of a polymeric material and, optimally, includes a lubricious material which defines the inner surface 55 and which aids the passage of an instrument through the inner tube lumen 31. Examples of suitable materials include polyethylene and nylon.

The reinforcing layer 51 can also be of different constructions and, in the form shown in FIGS. 4 and 5, includes a tightly wound coil spring. As shown in these figures, the spring is constructed of round or cylindrical wire and is tightly wound circumferentially so that the adjacent turns are in contact with each other. The reinforcing layer 51 extends from a location substantially at the distal end 33 proximally to a location closely adjacent the proximal section 43. This leaves only a short length of the tubular layer 49 between the proximal end of the reinforcing layer 51 and the juncture 46. Moreover, the proximal end of the reinforcing layer 51 is within the lumen 23 in the everted position of FIG. 4 so that, in this embodiment, the entire length of the tubular layer 49 which projects beyond the distal end 25 through the distal opening 27 is reinforced by the reinforcing layer 51. If desired, the reinforcing layer 51 can be shorter and in this event, a shorter length of the tubular layer 49 is reinforced by the reinforcing layer. However, at least the region of the tubular layer 49 which is adjacent the distal opening 27 of the catheter body 13 in the fully everted position of FIG. 4 is preferably reinforced by the reinforcing layer 51. In the inverted position, the reinforcing layer 51 extends completely through the curved distal end portion 29 of the catheter body 13.

To prevent movement of the ends of the reinforcing layer 51 axially relative to the tubular layer 49, annular beads of adhesive 57 may be applied to the opposite ends of the reinforcing layer 51 to thereby attach the reinforcing layer to the tubular layer 49. Of course, additional techniques, such as a friction fit and/or separate fasteners can be utilized to attach the layers 49 and 51 to each other.

In this embodiment, an end portion 58 of the everting element 21 is coupled by a polyimide sleeve 59 to the proximal section 43. The sleeve 59 is adhered to both the proximal section 43 and the everting element 21. A region 61 of the everting element 21 is heat shrunk over at least a portion of the reinforcing layer 51 and, in this embodiment, over the entire outer surface of the reinforcing layer. This provides a polymeric coating over the reinforcing layer which is continuous and smooths out the outer surface of the reinforcing layer. This smooth, continuous outer surface is much less likely to jump or "ratchet" over the edge of the distal opening 29 as the everting element 21 is everted and inverted. Alternatively, the end of the everting element 21 attached by the coupling sleeve 59 could be attached to a distal region of the reinforcing layer 51, and in this event, it would be preferred to provide a polymeric coating on the reinforcing layer by dipping or otherwise applying a polymeric layer of urethane or other suitable material over at least the outer surface of the reinforcing layer.

The catheter 11 can be used in a conventional manner. For example, with the everting element 21 in the inverted position of FIG. 5, the catheter 11 can be advanced using conventional techniques to a location within the body, such as through the cervix into the uterus to place the distal opening 27 into registry with an ostium of a fallopian tube (not shown). The everting element 21 is then everted by the application of fluid pressure to the chamber 35 and by controlling proximal movement of the inner tube 17 in a known manner to advance the everting element into the fallopian tube. The distal end portion 45 flexes as may be desired in moving through tortuous body areas, such as the fallopian tube, and the reinforcing layer 51 provides substantial strength against radial collapse or kinking. Accordingly, the inner tube lumen 31 remains open for drug infusion, aspiration and/or the insertion of any of a variety of medical instruments, including an endoscope.

The reinforcing layer 51 supports the tubular layer 49 against kinking in both the inverted and everted positions as the inner tube 17 is subjected to bending forces in curved body passages. As the distal end portion 45 of the inner tube 17 flexes to accommodate curved body passages, the coils of the reinforcing layer 51 on the outside of the curve may separate slightly, but this is insufficient to enable the distal end portion 45 to kink. Moreover, because the ends of the reinforcing layer 51 are trapped between the adhesive 57, the elongation of the reinforcing layer 51 on the outside of the curve can be no more than about the elongation of the tubular layer 49 along the outside of the curve. Consequently, the tubular layer 49 and the reinforcing layer 51 cooperate to provide much more rigidity to radial, inward loads than would be provided by any one of them while at the same time maintaining adequate flexibility.

Figure 6:
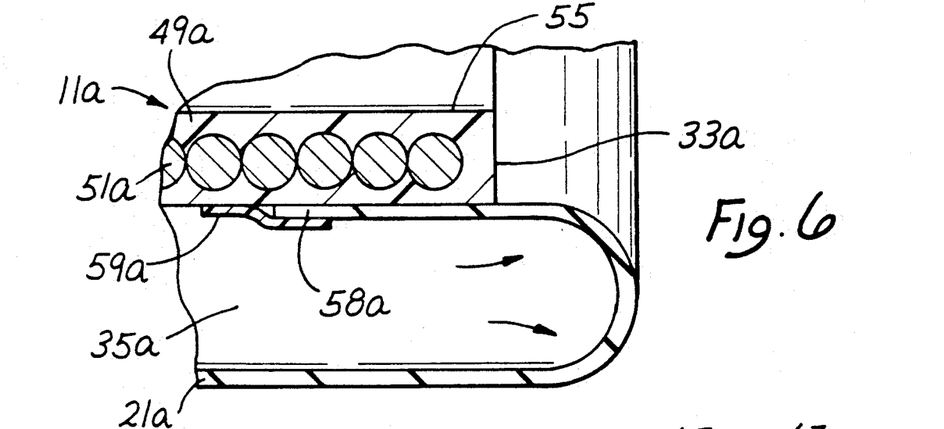
FIGS. 6-8 are enlarged, fragmentary sectional views of a distal region of the catheter taken on a longitudinal plane and showing different embodiments, respectively, of this invention.
Figure 7:
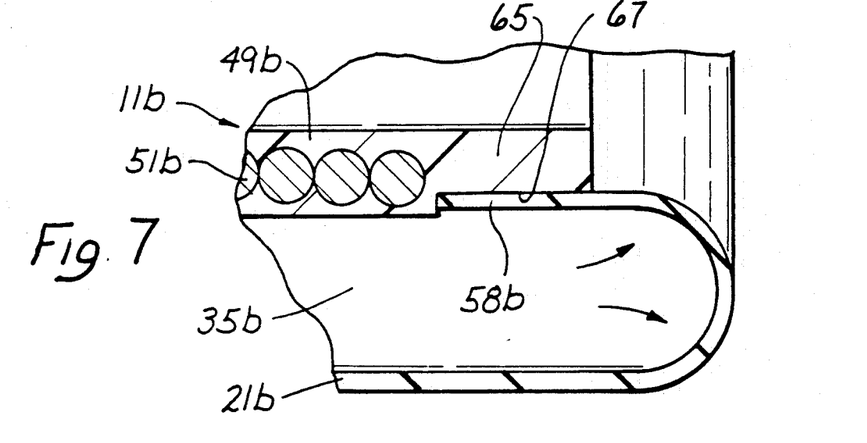
Figure 8:
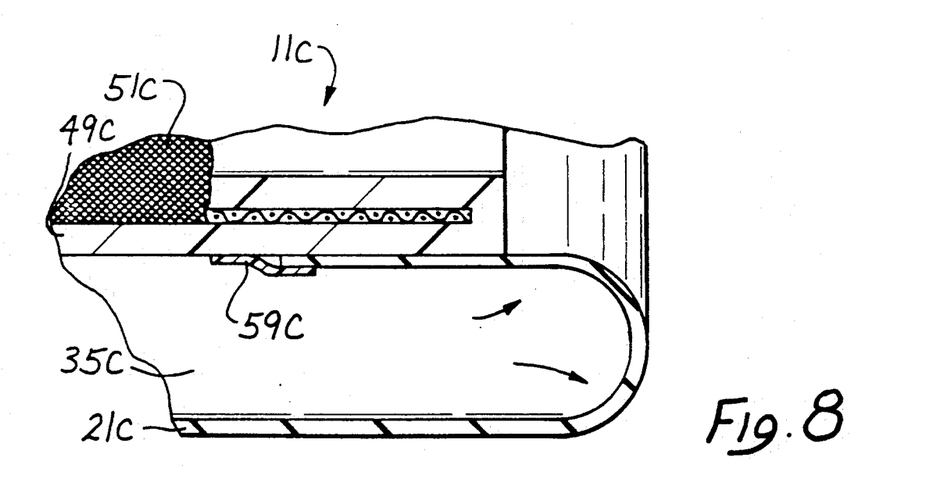

FIGS. 6-8 show catheters 11a-11c, respectively, each of which is identical to the catheter 11 in all respects not shown or described herein. Portions of the catheters 11a-11c corresponding to portions of the catheter 11 are designated by corresponding reference numerals followed by the letters "a", "b" and "c", respectively.

The primary differences between the catheter 11a of FIG. 6 and the catheter 11 is that the reinforcing layer 51a is embedded in the tubular layer 49a. As such, the tubular layer 49a also forms the polymeric layer over the outside of the reinforcing layer, and the reinforcing layer is encapsulated and captured within the tubular layer, which forms a matrix for the reinforcing layer. As with the catheter 11, the reinforcing layer 51a is in the form of a tightly wound coil spring of round wire.

A second difference between the catheters 11 and 11a is that the end portion 58a of the everting element 21a is coupled by the sleeve 59a to the tubular layer 49a closely adjacent the distal end 33a thereby saving some everting element material and eliminating the need to adhesively bond the sleeve to a stainless steel part.

The catheter 11b is identical to the catheter 11a, except that a section 65 of the tubular layer 49b extends distally beyond the distal-most turn of the reinforcing layer 51b to provide a location for attachment of the end portion 58b of the everting element 21b to the tubular layer. More specifically, the section 65 has an annular groove 67 in which the end portion 58b of the everting element 21b is seated. The sleeve 59 of the catheter 11 is eliminated, and the section 65 is adhered to the tubular layer 49b.

The catheter 11c is also identical to the catheter 11a, except that the reinforcing layer 51c is in the form of a braid embedded in the tubular layer 49c. The braid may comprise individual elongated filaments of various material, such as Kevlar or stainless steel, suitably braided together with at least one of the filaments extending circumferentially of the tubular layer 49c.

The catheter 11 also has engageable stops 71 and 73 (FIG. 9) to limit movement of the inner tube 17 proximally in the lumen 23 of the catheter body 13 so that the inner tube cannot be moved proximally sufficiently to rupture the everting element 21 or otherwise cause damage to the catheter 11. Although the stops can take different forms, in this embodiment, the stop 71 is in the form of a collar carried on the inner tube 17. The collar is sufficently small so that there is ample room around it in the lumen 23 for the passage of inflation media.

The stop 73 is carried within the fitting 15 and may be bonded to, or mechanically retained within, the fitting. More specifically, the stop 73 is mounted in a passage 75 of the fitting 15, and the stop 73 has an opening 77. The inner tube 17 extends through the passage 75 and the opening 77. However, the opening 77 is too small to permit the stop 71 to pass through it. Consequently, when the inner tube 17 is withdrawn sufficiently to bring the stop 71 into engagement with the stop 73, no further proximal movement of the inner tube is possible. The stops 71 and 73 engage before the inner tube 17 is withdrawn sufficiently to stretch the everting element.

Although exemplary embodiments of the invention have been shown and described, many changes, modifications and substitutions may be made by one having ordinary skill in the art without necessarily departing from the spirit and scope of this invention.

We claim:

1. A catheter comprising:
   an elongated catheter body having a lumen with a distal opening;
   an elongated inner tube having a flexible distal end portion and an inner tube lumen extending through the distal end portion of the inner tube, said inner tube being movable longitudinally in said lumen;
   a flexible everting element coupled to the catheter body and to the inner tube so that the everting element can be everted through the distal opening;
   said distal end portion of the inner tube including a flexible tubular layer and a flexible reinforcing layer which reinforces at least a region of the tubular layer and inhibits radial collapse of the inner tube lumen in at least a region of the distal end portion of the inner tube; and
   the reinforcing layer including at least one elongated element which extends circumferentially of the tubular layer.

2. A catheter as defined in claim 1 wherein the inner tube has a surface defining the inner tube lumen and the tubular layer includes lubricious material which defines at least a portion of said surface of said inner tube.

3. A catheter as defined in claim 1 wherein the tubular layer includes polymeric material.

4. A catheter as defined in claim wherein the reinforcing layer reinforces substantially the entire length of the distal end portion of the inner tube.

5. A catheter as defined in claim wherein the reinforcing layer includes a coil spring.

6. A catheter as defined in claim 1 wherein the reinforcing layer includes a braid.

7. A catheter as defined in claim 1 wherein the reinforcing layer surrounds the tubular layer.

8. A catheter as defined in claim 1 wherein the reinforcing layer is embedded in the tubular layer.

9. A catheter as defined in claim wherein the everting element can be inverted within the lumen of the catheter body and the catheter includes engageable stops to limit the movement of the inner tube proximally in the lumen of the catheter body so that the inner tube cannot be moved proximally sufficiently to rupture the everting element.

10. A catheter as defined in claim 9 wherein the catheter body has a proximal end portion, the catheter includes a fitting coupled to the proximal end portion of the catheter body, and one of said stops is carried by said fitting and another of said stops is carried by the inner tube.

11. A catheter comprising:
    an elongated catheter body having a lumen with a distal opening;
    an elongated inner tube having a flexible distal end portion and an inner tube lumen extending through the distal end portion of the inner tube, said inner tube being movable longitudinally in said lumen;
    a flexible everting element coupled to the catheter body and to the inner tube so that the everting element can be everted through the distal opening; and
    said distal end portion of the inner tube including a flexible inner tubular layer and a coil spring receiving the inner tubular layer.

12. A catheter as defined in claim 11 wherein the distal end portion of the inner tube includes a polymeric coating on at least a portion of the spring.

13. A catheter as defined in claim 12 wherein the polymeric coating includes a region of the everting element.

14. A catheter as defined in claim 11 wherein a region of the everting element is heat shrunk over at least a portion of the spring.

15. A catheter as defined in claim 11 wherein the inner tube includes a proximal section which is more rigid than the distal end portion and is attached to the distal end portion.

16. A catheter as defined in claim 11 including means for attaching the spring to the tubular layer.

17. A catheter as defined in claim 11 wherein the inner tube lumen has a smooth surface in said distal end portion which is defined by the tubular layer.

18. A catheter comprising:
   an elongated catheter body having a lumen with a distal opening;
   an elongated inner tube having a flexible distal end portion and an inner tube lumen extending through the distal end portion of the inner tube, said inner tube being movable longitudinally in said lumen;
   a flexible everting element coupled to the catheter body and to the inner tube so that the everting element can be everted through the distal opening to a fully everted position in which at least a major length of said distal end portion extends distally of said distal opening; and
   said distal end portion of the inner tube including a flexible tubular layer and a flexible reinforcing layer which reinforces the tubular layer adjacent the distal opening in said fully everted position and inhibits radial collapse of the inner tube lumen adjacent the distal opening in said fully everted position.

19. A catheter as defined in claim 18 wherein the reinforcing layer reinforces substantially the entire length of the distal end portion of the inner tube.

20. A catheter as defined in claim 18 wherein the reinforcing layer includes a coil spring.

21. A catheter as defined in claim 18 wherein the reinforcing layer includes a braid.

* * * * *

UNITED STATES PATENT AND TRADEMARK OFFICE
CERTIFICATE OF CORRECTION

PATENT NO. : 5,171,305

DATED : December 15, 1992

INVENTOR(S) : David P. Schickling et al

It is certified that error appears in the above-identified patent and that said Letters Patent is hereby corrected as shown below:

Column 3, line 52, after "Fig." insert -- 1 -- .

Column 8, line 30, after "Claim" insert -- 1 -- .

Column 8, line 33, after "Claim" insert -- 1 -- .

Column 8, line 41, after "Claim" insert -- 1 -- .

Signed and Sealed this

Twenty-sixth Day of October, 1993

Attest:

BRUCE LEHMAN

Attesting Officer

Commissioner of Patents and Trademarks